(12) United States Patent
Schabbach et al.

(10) Patent No.: US 11,376,370 B2
(45) Date of Patent: Jul. 5, 2022

(54) ELECTRONICS FOR DOSAGE SENSING

(71) Applicant: SANOFI, Paris (FR)

(72) Inventors: Michael Schabbach, Frankfurt am Main (DE); Michael Meissner, Bridgewater, NJ (US)

(73) Assignee: Sanofi, Paris (FR)

(*) Notice: Subject to any disclaimer, the term of this patent is extended or adjusted under 35 U.S.C. 154(b) by 176 days.

(21) Appl. No.: 16/619,668

(22) PCT Filed: Jun. 5, 2018

(86) PCT No.: PCT/EP2018/064686
§ 371 (c)(1),
(2) Date: Dec. 5, 2019

(87) PCT Pub. No.: WO2018/224460
PCT Pub. Date: Dec. 13, 2018

(65) Prior Publication Data
US 2020/0164154 A1    May 28, 2020

(30) Foreign Application Priority Data
Jun. 9, 2017  (EP) ..................................... 17305693

(51) Int. Cl.
*A61M 5/315*     (2006.01)
*A61M 5/24*      (2006.01)
(Continued)

(52) U.S. Cl.
CPC .......... *A61M 5/31568* (2013.01); *A61M 5/24* (2013.01); *A61M 5/3293* (2013.01);
(Continued)

(58) Field of Classification Search
CPC .. A61M 5/31568; A61M 5/24; A61M 5/3293; A61M 2205/3306;
(Continued)

(56) References Cited

U.S. PATENT DOCUMENTS

| 8,945,066 B2* | 2/2015 | Bochenko ............... A61M 5/31 604/189 |
| 2015/0085286 A1* | 3/2015 | Whalley ............. A61M 5/1689 356/434 |

(Continued)

FOREIGN PATENT DOCUMENTS

| JP | 2013-505433 | 2/2013 |
| JP | 2015-518747 | 7/2015 |

(Continued)

OTHER PUBLICATIONS

International Preliminary Report on Patentability in Application No. PCT/EP2018/064686, dated Dec. 10, 2019, 9 pages.

(Continued)

*Primary Examiner* — Lauren P Farrar
(74) *Attorney, Agent, or Firm* — Fish & Richardson P.C.

(57) ABSTRACT

An injection device includes a cartridge configured to hold a volume of fluid, the cartridge having a proximal end and a distal end through which the fluid is dispensed; a stopper disposed in the cartridge and configured to move from the proximal end toward the distal end to cause the fluid to be dispensed through the distal end of the cartridge; and an electronic device disposed at the distal end of the cartridge, the electronic device including an emitter configured to transmit a signal toward the stopper, a receiver configured to (Continued)

receive reflections of the signal from the stopper, and a controller configured to wirelessly transmit data related to a position of the stopper in the cartridge.

25 Claims, 7 Drawing Sheets

(51) Int. Cl.
*A61M 5/32* (2006.01)
*G01F 11/02* (2006.01)
*G01F 22/00* (2006.01)

(52) U.S. Cl.
CPC ............ *G01F 11/021* (2013.01); *G01F 22/00* (2013.01); *A61M 2205/3306* (2013.01); *A61M 2205/3375* (2013.01); *A61M 2205/3389* (2013.01); *A61M 2205/52* (2013.01); *A61M 2205/8206* (2013.01)

(58) Field of Classification Search
CPC .. A61M 2205/3375; A61M 2205/3389; A61M 2205/52; A61M 2205/8206; A61M 2205/3553; A61M 2205/50; A61M 2005/2485; A61M 5/3129; A61M 5/16886; A61M 5/20; G01F 11/021; G01F 22/00
See application file for complete search history.

(56) References Cited

U.S. PATENT DOCUMENTS

| 2015/0174342 A1* | 6/2015 | Mitrosky ............... G01F 11/027 604/506 |
| 2015/0289896 A1 | 10/2015 | Gomi et al. |
| 2017/0312430 A1* | 11/2017 | Schleicher .......... A61M 5/1723 |
| 2017/0312455 A1 | 11/2017 | Mirov et al. |
| 2017/0316177 A1 | 11/2017 | Mirov et al. |

FOREIGN PATENT DOCUMENTS

| JP | 2015-529481 | 10/2015 |
| KR | 10-2016-0053322 | 5/2016 |
| WO | WO 2013/054165 | 4/2013 |
| WO | WO 2014/009442 | 1/2014 |
| WO | WO 2014/145906 | 9/2014 |
| WO | WO 2017/189129 | 11/2017 |
| WO | WO 2017/189153 | 11/2017 |
| WO | WO 2017/189970 | 11/2017 |

OTHER PUBLICATIONS

International Search Report and Written Opinion in Application No. PCT/EP2018/064686, dated Jul. 2, 2018, 11 pages.

* cited by examiner

ELECTRONICS FOR DOSAGE SENSING

CROSS REFERENCE TO RELATED APPLICATIONS

The present application is the national stage entry of International Patent Application No. PCT/EP2018/064686, filed on Jun. 5, 2018, and claims priority to Application No. EP 17305693.8, filed on Jun. 9, 2017, the disclosures of which are incorporated herein by reference.

TECHNICAL FIELD

This disclosure relates to an injection device and to an electronic component of an injection device for sensing a dosage of a medicament to be administered.

BACKGROUND

A variety of diseases exist that require treatment by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use.

SUMMARY

Among other things, the disclosure describes a drug injector that includes a sensing system for determining a dosage of a medicament in a cartridge in the delivery device.

In one aspect, an injection device includes a cartridge configured to hold a volume of fluid. The cartridge has a proximal end and a distal end through which the fluid is dispensed. The injection device also includes a stopper disposed in the cartridge and configured to move from the proximal end to the distal end to cause the fluid to be dispensed through the distal end of the cartridge. The injection device also includes an electronic device disposed at the distal end of the cartridge or, alternatively, cartridge housing. The electronic device includes an emitter configured to transmit a signal toward the stopper and a receiver configured to receive reflections of the signal from the stopper. The electronic device also includes a controller configured to wirelessly transmit data related to a position of the stopper in the cartridge.

The details of one or more embodiments are set forth in the accompanying drawings and the description below. Other features, objects, and advantages will be apparent from the description and drawings, and from the claims.

BRIEF DESCRIPTION OF THE FIGURES

Like reference symbols in the various drawings indicate like elements.

DETAILED DESCRIPTION

Figure 1:
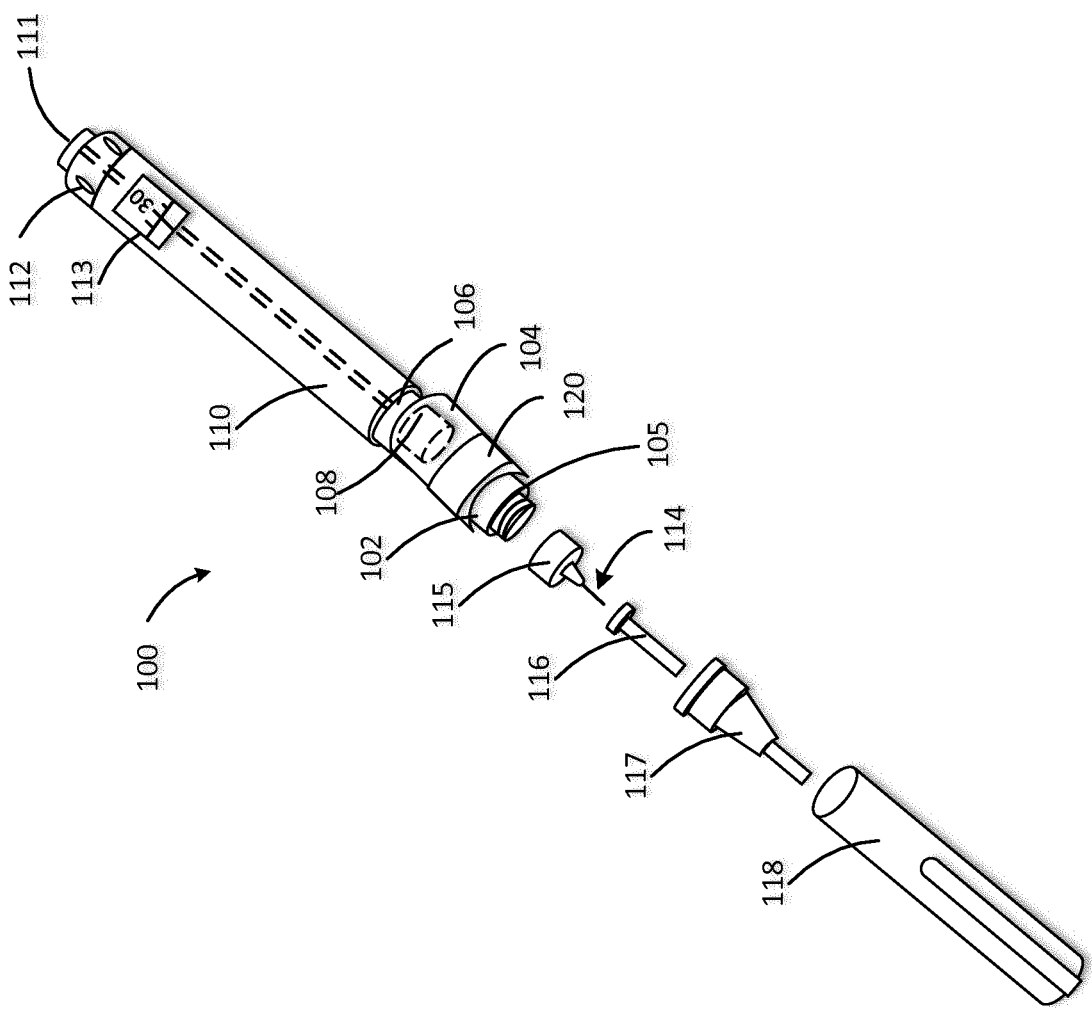
FIG. 1 is an exploded view of an example of an injection device including an electronic measurement device, according to embodiments of the present disclosure.

A drug delivery device may include an electronic device which may include a sensing system for determining a dosage of a medicament in a cartridge in the delivery device. The sensing system may include an emitter and a receiver, the emitter configured to bounce a signal off of a stopper in the cartridge and the receiver configured to receive a reflection of the signal. Based on a parameter of the reflected signal, a processor may determine a position of the stopper in the cartridge. Based on the geometry of the cartridge, a processor may compute a dosage of the medicament that has been dispensed based on the position of the stopper.

The subject matter described herein will largely be described with reference to a drug delivery device such as an injection device (e.g., an insulin injection device). However, the systems and techniques described herein are not limited to such applications, and may be deployed with injection devices that eject other medicaments, or with other types of medical devices (e.g., pumps).

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 18-20° C.), or refrigerated temperatures (e.g., from about 4-8° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

FIG. 1 is an exploded view of an example of an injection device 100 according to embodiments of the present disclosure. The injection device 100 may be a pre-filled, disposable or reusable injection pen. The injection device 100 includes a housing 110 that contains a cartridge 102. The cartridge 102 is configured to hold a volume of fluid. In some embodiments, the cartridge 102 is a medicament container, such as an insulin container. The cartridge 102 includes a distal end 105 and a proximal end 106. In some embodiments, the proximal end 106 of the cartridge 102 may reside within the housing 110 of the injection device 100 and therefore may not be readily visible.

The injection device 100 includes a stopper 108 that is disposed in the cartridge 102. The stopper 108 is configured to move from the proximal end 106 of the cartridge 102 toward the distal end 105 of the cartridge 102 to cause the fluid to be dispensed through the distal end 105 of the cartridge 102. The injection device 100 also includes a needle hub 115 that is disposed at the distal end 105 of the cartridge 102. A needle 114 can be affixed to the needle hub 115 proximate to the aperture 119 such that the fluid travels through the aperture 119 and the needle 114 when dispensed. In some embodiments, the needle hub 115 and the needle 114 are threaded such that the needle 114 can be screwed onto the needle hub 115 or the needle hub 115 can be screwed onto the needle 114. The needle 114 is protected by an inner needle cap 116 and an outer needle cap 117, which in turn can be covered by a cap 118.

A drug dose (e.g., such as an insulin dose) to be ejected from injection device 100 can be selected by turning a dosage knob 112, and the selected dose can then be displayed by a dosage window 113. In some examples, the dosage window 113 is a display, such as an electronic display. In some examples, the selected dose can be displayed in multiples of International Units (IU), wherein one IU is the biological equivalent of about 45.5 micrograms of medicament such as pure crystalline insulin (e.g., 1/22 mg). An example of a selected dose displayed in the dosage window 113 may, for example, be 30 IUs, as shown in FIG. 1A. In some examples, the selected dose may be displayed differently, for example, by an electronic display. In some examples, the dosage window 113 relates to the section of the injection device through or on which the selected dosage is visible.

Turning the dosage knob 112 may cause a mechanical click sound to provide acoustical feedback to a user. The numbers displayed in the dosage window 113 are printed on a sleeve that is contained in housing 110 and mechanically interacts with a piston in the cartridge 102. When the needle 114 is inserted into a skin portion of a patient, and then an injection button 111 is pushed, the medicament is ejected from the injection device 100. Ejection of the dose may also cause a mechanical click sound. Such a mechanical click sound may be different from the sounds produced when the dosage knob 112 is turned.

The injection device 100 may be used for several injection processes until either the cartridge 102 is empty or the expiration date of the injection device 100 is reached. In some examples, before using the injection device 100 for the first time, it may be necessary to perform a "prime shot" to remove air from the cartridge 102 and the needle 114, for example, by selecting two units of medicament and pressing the injection button 111 while holding the injection device 100 with the needle 114 oriented upwards.

The injection device 100 is configured to determine the volume of medicament fluid (e.g., insulin) in the cartridge 102, which can represent the dosage of medicament to be administered to the patient. For example, the injection device includes an electronic device 120 configured to measure a position of the stopper 108. The electronic device 120 includes an emitter 202 and a receiver 204 (shown in FIG. 2) In some embodiments, one or both of the emitter 202 and the receiver 204 may be disposed in the cartridge housing 104. The cartridge 102 and/or the cartridge housing 104 may be made from and/or include a material that allows the one or more waves emitted by the emitter and the reflections of the one or more waves to pass therethrough (or, e.g., pass substantially therethrough).

Figure 2:
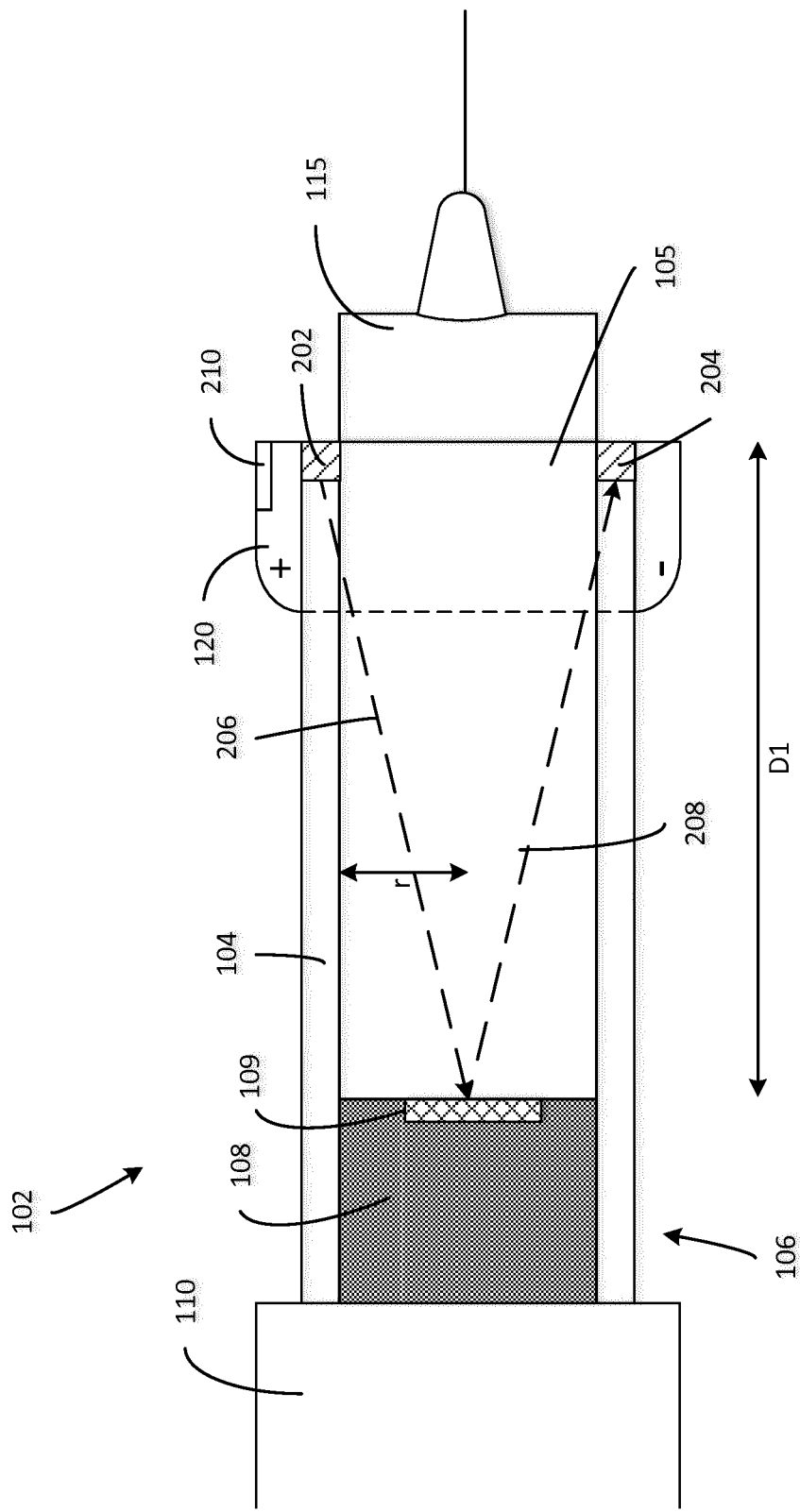
FIG. 2 is a cross-sectional view of an example of an injection device that includes an electronic measurement device, according to embodiments of the present disclosure.

Referring to FIG. 2, the emitter 202 is configured to transmit one or more signals 206 toward the proximal end 106 of the cartridge 102 where the one or more waves are reflected from the proximal end 106 of the cartridge 102 back to the receiver 204 located at the distal end (e.g., by bouncing off a surface of the stopper 108, as described in detail below). The receiver 204 is configured to receive reflections 208 of the signal. Information related to the transmitted signal 206 and the reflections 208 of the one or more transmitted signals can be used to determine the volume of the fluid in the cartridge 102. For example, the information related to the one or more transmitted signals 206 and the reflections 208 of the one or more waves can be used to determine a distance traveled by the transmitted signal 206. The distance traveled by the transmitted signal 206 can be used to determine a volume of the fluid in the cartridge 102, and the volume of the fluid in the cartridge 102 can be used to determine a dose of medicament administered to a patient. In some embodiments, both the emitter 202 and the receiver 204 are included as components of a single transceiver package. The one or more signals may include acoustic waves, ultrasonic waves, light waves, or any combination thereof.

In some embodiments, the information related to the one or more transmitted signals 206 (e.g., times of transmission, intensity at transmission) and the reflections 208 of the one or more transmitted signals (e.g., times of receipt, intensity at receipt) is provided to and/or received by a computing device (e.g., the computer system 600 of FIG. 6), and the computing device uses such information to determine the volume of the fluid in the cartridge 102. In some examples, the emitter 202 is an acoustic (e.g., ultrasonic) transmitter that is configured to transmit one or more acoustic waves (e.g., ultrasonic waves) toward the proximal end 106 of the cartridge 102, and the receiver 204 is an acoustic receiver that is configured to receive reflections of the one or more acoustic waves. The computing device can identify times at which each acoustic wave is transmitted, and for each transmitted acoustic wave, times as which the corresponding reflection is received by the receiver 204. With the acoustic wave velocity being known (e.g., in this case, the speed of sound), the elapsed time between transmission and receiving of the wave, sometimes referred to as time of flight (TOF), can be used to determine the distance traveled by the wave.

The distance traveled by the wave represents the distance from the emitter 202, to the reflection surface (e.g., a surface of the stopper 108), to the receiver 204. This distance can be divided by two to determine the distance between the stopper 108 and the receiver 204. Because the stopper 108 defines the boundary of the fluid near the proximal end 106 of the cartridge 102, the determined distance represents a length of the cartridge 102 within which the fluid resides. The determined distance, along with the known dimensions of the cartridge 102, can be used to determine the volume of the fluid in the cartridge 102. For example, for a cylindrical cartridge, the volume of fluid (V) in the cartridge 102 is defined by the equation:

$$V = \pi \ast r^2 \ast D_1$$

where r is the internal radius of the cartridge and D1 is the distance from the surface of the stopper 108 to the distal end 105 of the cartridge 102.

In an example, the emitter 202 transmits an acoustic wave at a first time $t_1$. The first time $t_1$ (e.g., the transmission time of the acoustic wave) is provided to the computing device. The acoustic wave propagates from the emitter 202 toward the proximal end 106 of the cartridge 102 and is reflected off of (e.g., bounces off of) the stopper 108. A reflection 208 of the acoustic wave (e.g., a reflected wave) propagates from the stopper 108 toward the receiver 204. The reflected wave is received at a second time $t_2$. The speed of the acoustic wave is the speed of sound in the liquid. The elapsed time between transmission and receiving of the acoustic wave is $t_2 - t_1$. The elapsed time is multiplied by the speed of sound to determine the distance traveled by the wave from the emitter 202, to the distal end 105 of the cartridge 102, back to the receiver 204. The distance traveled is divided by two to determine the distance between the emitter 202/the receiver 204 and the stopper 108. The volume of fluid in the cartridge 102 (e.g., the volume of fluid enclosed in the cartridge 102 between the stopper 108 and the distal end 105) is determined by multiplying the determined distance by the cross-sectional area of the cartridge 102. The determined volume of fluid in the cartridge 102 is the dose that is to be administered to the patient.

In some embodiments, the stopper 108 includes a reflective material 109 that is disposed at an end of the stopper 108 that faces the emitter 202. The reflective material 109 is configured to improve the signal quality of the reflected signal (e.g., by minimizing signal loss upon reflection, reducing noise in the signal, improving signal to noise ratio, etc.), thereby improving the TOF calculation.

Referring generally to FIGS. 1-2 and 4A-4B, in some embodiments, the emitter 202 is a light source that is configured to transmit light toward the stopper 108, and the receiver 204 is a light receiver that is configured to receive reflections or remission of the light waves. In some examples, the cartridge housing 104 may be made from and/or include a material that allows the light waves and the reflections of the light waves to pass therethrough (or, e.g., pass substantially therethrough). In some embodiments, the cartridge 102 includes a transparent material, such as one or both of glass and plastic.

While the injection device 100 has been largely described as being configured to determine the volume of the fluid in the cartridge 102 using information related to the one or more transmitted signals and the reflections of the one or more signals, in some embodiments, the injection device 100 may include one or more components other than or in addition to the emitter 202 and receiver 204 for determining the volume of the fluid.

In some embodiments, the volume of the fluid in the cartridge 102 may be determined continuously as the fluid is dispensed from the injection device 100. For example, when the injection button 111 is pushed and as the medicament is ejected from the cartridge 102, the injection device 100 may continuously determine the volume of the fluid in the cartridge 102 such that the user can receive continuous feedback of the current volume of fluid in the cartridge 102.

In particular, in a manner substantially similar to that described above with respect to FIG. 2, information related to one or more transmitted signals (e.g., times of transmission) and the reflections of the one or more transmitted signals (e.g., times of receipt) can be provided to and/or received by the computing device. The elapsed time between transmission and receiving of the signal (e.g., the TOF) can be multiplied by the speed of the signal (e.g., the speed of sound) to determine the distance traveled by the wave. The distance traveled by the wave represents the distance from the emitter 202, to the stopper 108, and back to the receiver 204. The distance traveled is divided by two to determine the distance between the emitter 202/the receiver 204 and the stopper 108. The volume of fluid in the cartridge 102 (e.g., the volume of remaining fluid enclosed in the cartridge 102 between the stopper 108 and the distal end 105) is determined by multiplying the determined distance by the cross-sectional area of the cartridge 102. The determined volume of fluid in the cartridge is the dose that is remaining in the cartridge 102 which is yet to be administered to the patient. The volume of fluid in the cartridge 102 can be continuously determined such that the remaining dosage is known throughout administration. Computing a dosage may be accomplished by a microcontroller 210 on board the injection device 100 or may be accomplished by an external computer system 600. In some implementations, another kind of processor can be used in place of the microcontroller 210 on board the injection device 100.

Figure 3:
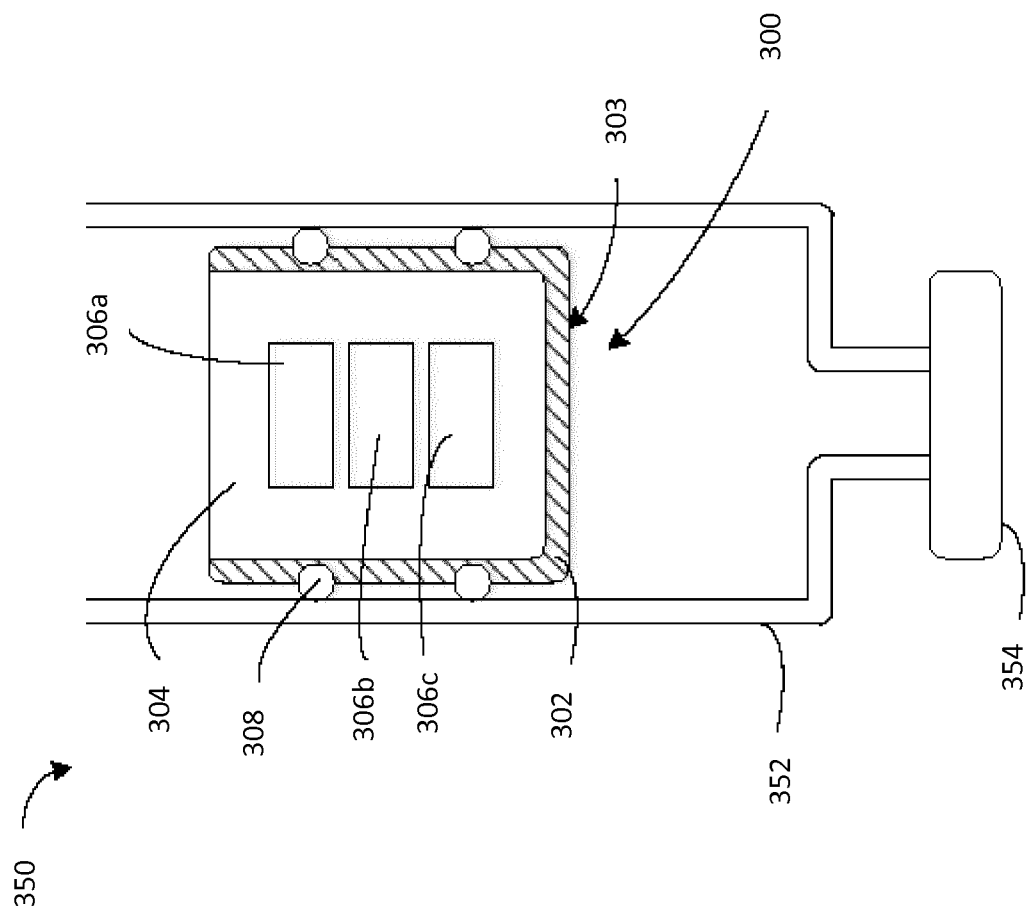
FIG. 3 is a cross-sectional view of an example of a stopper disposed within a cartridge where the stopper includes embedded electronic devices, according to embodiments of the present disclosure.

FIG. 3 is a cross-sectional view of a stopper 300 disposed in a cartridge 350. The stopper includes embedded electronic components 306a, 306b, and 306c. The stopper 300 has a shell 302 and a core 304 with electronic devices 306a, 306b, and 306c embedded in the core 304. Optional integrated sealing element 308 can be configured to provide a sealing interface with the cartridge upon the stopper's introduction into the cartridge 350. In some instances, the shell 302 provides a rigid surface for interfacing with a head of a plunger. In this way, the shell 302 protects the electronics devices 306a, 306b, 306c from getting deformed by a push of a plunger on the stopper 300 as the stopper 300 is forced to move along the length of the cartridge 350. In some instances, the shell 302 has heat-resistant properties which may shield the electronic components 306a, 306b, and 306c from heat produced during a heat sterilization process to sterilize the stopper 300 and the cartridge 350. It is also contemplated that the shell and core be made of rigid or soft materials in various combinations to withstand high temperatures used during sterilization processes, while providing structure and support for the electronics and plunger. Alternatively, the shell/core can be made of one unitary piece with the electronics molded therein.

It is contemplated that the waves emitted by the emitter can be optical, acoustic or ultrasonic in nature. In an example, a transmitter 306c transmits an acoustic wave at a first time t1. The first time t1 (e.g., the transmission time of the acoustic wave) may be provided to an external device (e.g. a controller) via a wireless transmission by a wireless transceiver 306b. The transmitter 306c and the wireless transceiver 306b may be powered by a power source 306a. The acoustic wave propagates from the transmitter in the stopper 300 toward the distal end (the end nearest the cap 354) of the cartridge 350 and is reflected off of (e.g., bounces off of) a surface of the cartridge 350 or a reflector (not shown). A reflection of the acoustic wave (e.g., a reflected wave) propagates from the distal end of the cartridge 350 toward a sensor in the stopper 300. The reflected wave is received at a second time t2. The speed of the acoustic wave is the speed of sound in the medicament in the cartridge (e.g., 1484 meters per second in water). The elapsed time between transmission and receiving of the acoustic wave is t2−t1. The elapsed time is multiplied by the speed of sound to determine the distance traveled by the wave from the transmitter, to the distal end of the cartridge 350, back to the sensor. The distance traveled is divided by two to determine the distance between the stopper 300 and the distal end of the cartridge 350. The volume of medicament in the cartridge 350 (e.g., the volume of medicament enclosed in the cartridge 350 between the stopper 300 and the distal end) is determined by multiplying the determined distance by the cross-sectional area of the cartridge 350. The determined volume of medicament in the cartridge 350 is the dose that is to be administered to the patient.

Referring generally to the embodiments shown in FIGS. 1-2 and 4A-4B, signal transmission occurs in the opposite direction (e.g. from distal end 105 toward proximal end 106 and bouncing back) as the signals are emitted by emitter 202 and reflections of the signals are received by receiver 204. This is advantageous as the stopper 108 provides a flat surface substantially equal to the cross-section of the cartridge off of which the signal may reflect (e.g. bounce back) toward the receiver. It has been found that in alternative configurations, where the emitter and receiver are placed at the proximal end and the waves bounce off the distal end, the shape and configuration of the cartridge may not provide a substantially flat surface for the waves to bounce off of. Thus, locating the emitter and receiver at the distal end, near the neck of the cartridge and allowing the waves to bounce off the substantially flat surface of the stopper leads to greater accuracy of measurements. It is also advantageous to include electronic components outside of the stopper as the cartridge may be heat sterilized without regard to damaging electronic components embedded in a stopper with the high heat. As the electronic components are located external to the stopper, the design and manufacturing of the stopper is simpler.

Figure 4A:
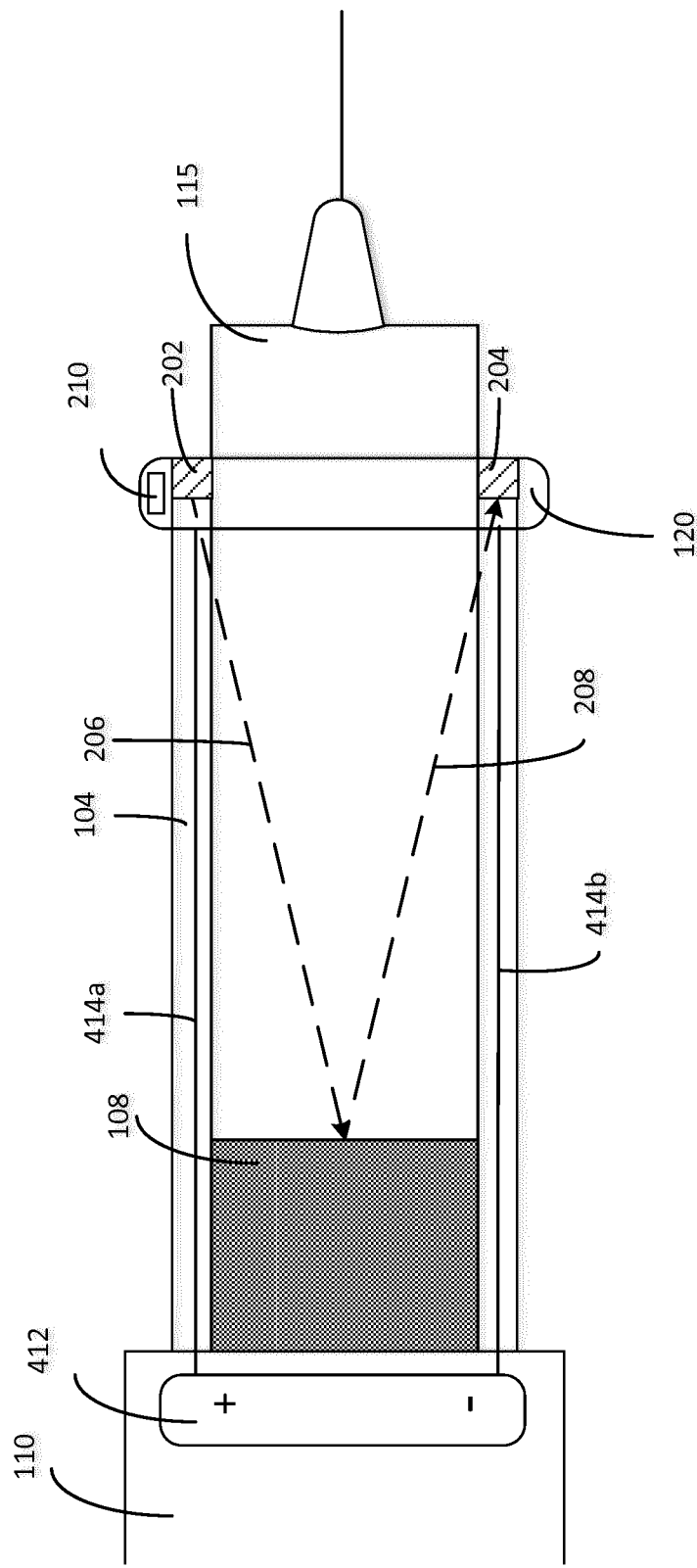
FIG. 4A is a cross-sectional view of an example of an injection device that includes an electronic measurement device with a battery disposed in the injector housing, according to embodiments of the present disclosure.

FIG. 4A is an embodiment of an electronic device 120 including an emitter 202, a receiver 204, and an energy source 412. In this embodiment, the energy source 412 is located in the housing 110 of the injection device. The energy source 412 is electrically connected to the emitter 202 and receiver 204 by electronic leads 414a and 414b. The energy source may include a battery. The electronic leads 414a and 414b run through the cartridge housing 104. The electronic leads 414a and 414b allow the energy source 412 to power the emitter 202, the receiver 204, and the microcontroller 210.

The microcontroller 210 includes a wireless transceiver which may communicate using any known wireless communication technique including, for example Bluetooth, NFC, or radio frequencies. The microcontroller 210 may communicate data relating to the state of the cartridge or signals received at the receiver 204 to an external database. The state of the cartridge may correspond to, for example, a fill level of medicament in the cartridge or a position of the stopper. The state of the cartridge may allow measurement of an injected dose of medicament.

The communication with the microcontroller 210 can be one way or bidirectional. In some instances, data transferred from the sensor device to an external data base contains information which is related to the identity of the device e.g. a unique number, calibration data, production lot information, device material information, data related to storage time and production time, and information related to the sensor measurement (e.g., time of measurement, sensor measurement results like temperature, distances, light signals, acoustic signals). In some instances, data coming from the external data base device to the microcontroller 210 contains information regarding "wake up" signals, triggers to measure, time information, or calibration data.

Figure 5:
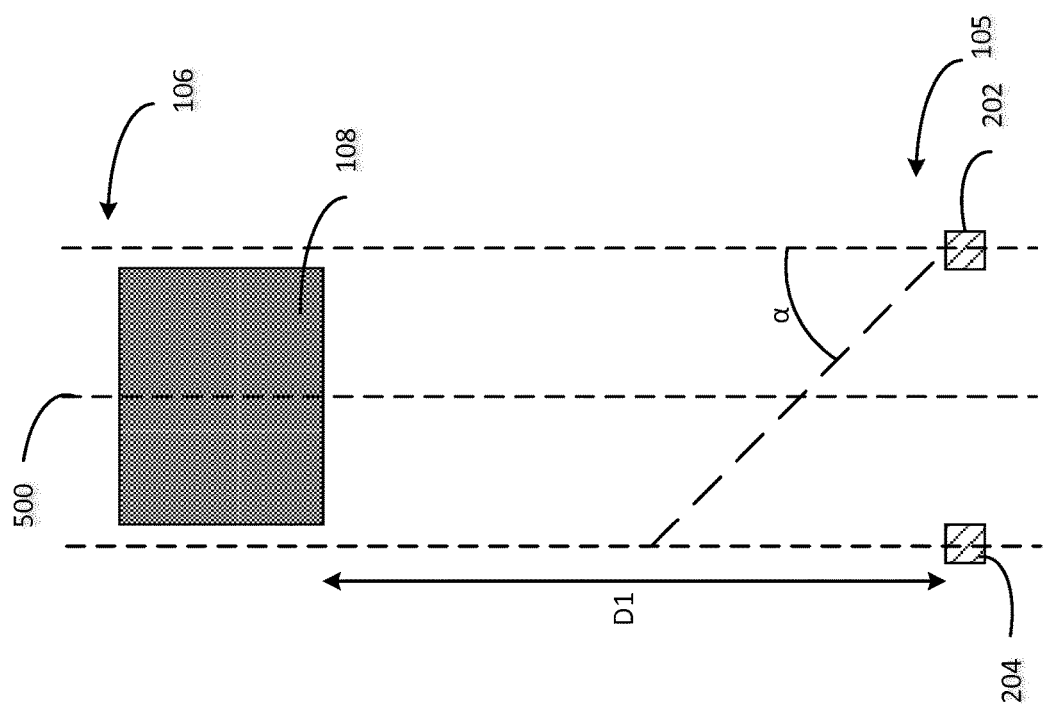
FIG. 5 is a schematic showing the relative positioning of an emitter, a receiver, and a stopper in an example injection device according to embodiments of the present disclosure.

FIG. 5 is a schematic showing the relative position of a stopper 108, an emitter 202 and a receiver 204 in relation to a longitudinal axis 500. The emitter 202 is configured to be able to emit a signal at an angle of between 0° and α. Accordingly, the receiver 204 is configured to be able to receive a reflection of a signal after bouncing off of the stopper 108 at an angle of between 0° and α. As the stopper 108 moves through the distance D1 from the proximal end 106 toward the distal end 105, the emitter 202 and the receiver 204 has a range that enables them emit and capture the signals and reflections, respectively. In some embodiments, α is between 0 and 90°. In other embodiments, it's between 20 and 70° degrees. In yet other embodiments, it is between 55 and 65°.

Figure 4B:
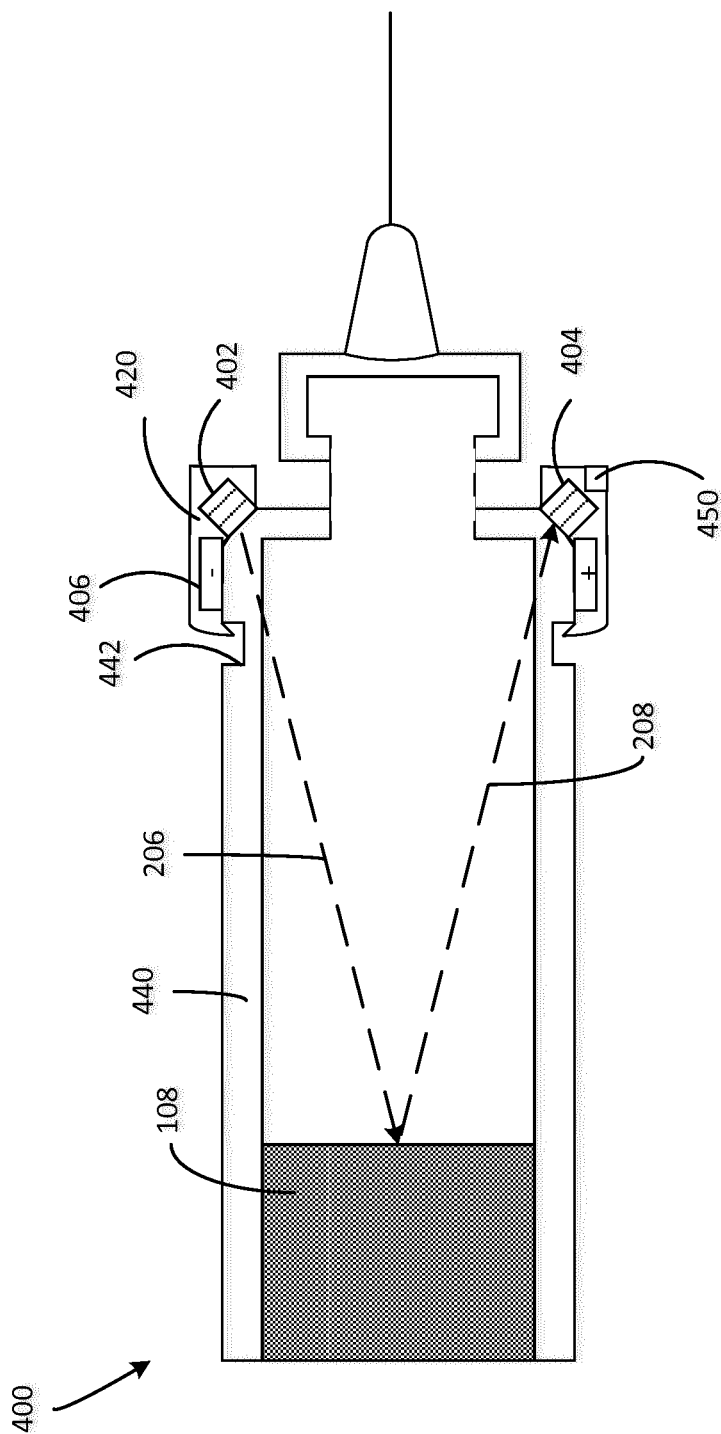
FIG. 4B is a cross-sectional view of an example of an injection device assembly with a detachable electronic measurement device, according to embodiments of the present disclosure.

FIG. 4B is an embodiment of an electronic device 420 which is detachable from a cartridge 400 or a cartridge housing 440. The emitter 402 and the receiver 404 are positioned in the detachable electronic device 420 so they can emit and receive signals and reflections of signals through a portion of the cartridge housing 440, respectively. The cartridge housing 440 is typically transparent to the signals 206 emitted from the emitter 402 and the reflections of the signals 208 received by the receiver 404. In some embodiments, the cartridge housing 440 is transparent to an light signal, an ultrasonic signal, and/or an acoustic signal.

The cartridge housing 440 includes a ridge 442 such that a clasp or snap portion of the electronic device 420 may interface with the ridge 442 and secure the electronic device 420 to the cartridge housing 440. As the electronic device 420 may be attached and detached from the cartridge housing 440, it may be calibrated upon attachment to the cartridge housing 440. The calibration process typically enables the emitter and receiver to accurately determine the position of the stopper 108 within the cartridge 400. The microcontroller 450 may include a memory storage medium (also referred to as a "memory" herein) that stores information relating to the medicament useful for calibration and dosing information.

The emitter 402 and the receiver 404 are positioned in the detachable electronic device 420 such that, when the detachable electronic device 420 is attached to the cartridge housing 440, the emitter 402 and the receiver 404 are positioned such that the emitter is able to emit a signal at an angle of between 0° and a in relation to the longitudinal axis of the cartridge. Accordingly, the receiver 404 is able to receive a reflection of a signal after bouncing off of the stopper 108 at an angle of between 0° and α. In some embodiments, α is between 0 and 90°. In other embodiments, it's between 20 and 70° degrees. In yet other embodiments, it is between 55 and 65°. Calibration may be necessary to ensure proper positioning of the emitter 402 and the receiver 404 upon attaching the detachable electronic device 420 to the cartridge housing 440.

Figure 6:
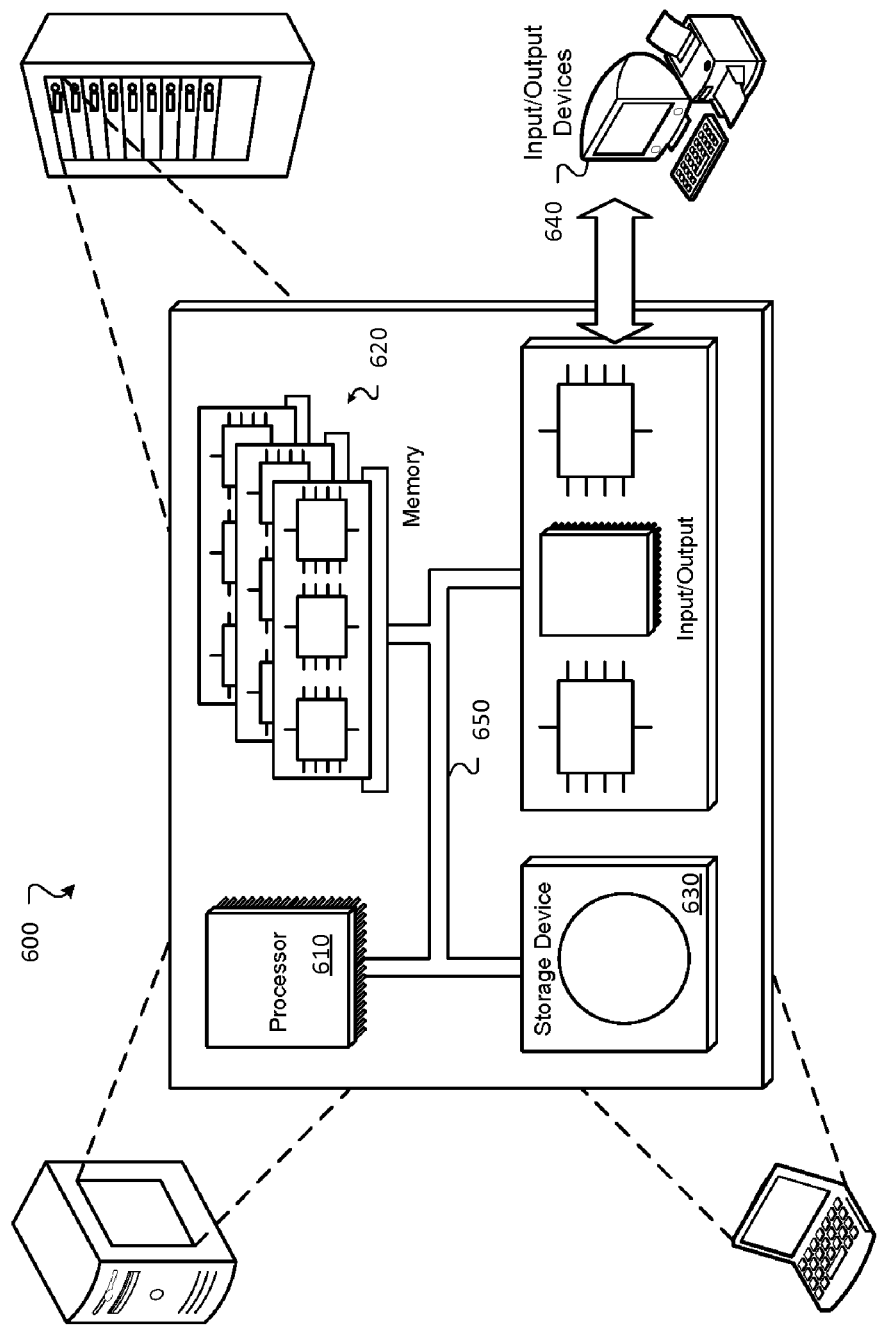
FIG. 6 is a block diagram of an example computer system of an example injection device according to embodiments of the present disclosure.

FIG. 6 is a block diagram of an example computer system 600. For example, the computer system 600 may be incorporated into the injection device 100 of FIGS. 1-4, and/or the injection device 100 may be configured to interact with a separate computer system 600 (e.g. via microcontroller 210 shown in FIG. 2). The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. The processor 610 can be a single-threaded processor, a multi-threaded processor, or a quantum computer. The processor 610 is capable of processing instructions stored in the memory 620 or on the storage device 630. The processor 610 may execute operations such as causing the injection device 100 to carry out one or more of the operations described above to determine the volume of the fluid in the cartridge 102.

A portable computing device such as a smartphone or tablet computer may be an example of the computer system 600. In some implementations, the portable computing device runs an application for interfacing with the electronic device 120 on the injection device 100. For example, the portable computing device may communicate with the electronic device 120 using one or more computer networks (e.g., wireless or wired communication networks, or a combination of the two), such the application running on the portable computing device can display information based on data received from the electronic device 120. In some implementations, other types of computer systems may display information based on data received from the electronic device 120. In some implementations, "cloud" computing techniques are used to communicate information between the portable computing device and the electronic device 120. For example, both the portable computing device and the electronic device 120 may communicate with one or more cloud servers (which may be other examples of computer systems 600) that act as intermediate data processing and storage facilities. A cloud computing system may also provide access, via a portable computing device, to externally stored patient, dosage, or other data.

The memory 620 stores information within the system 600. In some embodiments, the memory 620 is a computer-readable medium. The memory 620 can, for example, be a volatile memory unit or a non-volatile memory unit. In some embodiments, the memory 620 stores information related to one or more of the velocity of the one or more waves transmitted by the emitter 202, the dimensions of the cartridge 102, and data that can be used to correlate the applied voltage across the electrodes 202, 204 to a distance between the electrodes 202, 204.

The storage device 630 is capable of providing mass storage for the system 600. In some embodiments, the storage device 630 is a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network. In some embodiments, the information stored on the memory 620 can also or instead be stored on the storage device 630.

The input/output device 640 provides input/output operations for the system 600. In some embodiments, the input/output device 640 includes one or more of network interface devices (e.g., an Ethernet card), a serial communication device (e.g., an RS-232 port), and/or a wireless interface device (e.g., a short-range wireless communication device, an 802.11 card, a 3G wireless modem, or a 4G wireless modem). In some embodiments, the input/output device 640 includes driver devices configured to receive input data and send output data to other input/output devices, e.g., a keyboard, a printer, and display devices (e.g., such as the dosage window 113). In some embodiments, mobile computing devices, mobile communication devices, and other devices are used.

In some embodiments, the system 600 is a microcontroller. A microcontroller is a device that contains multiple elements of a computer system in a single electronics package. For example, the single electronics package could contain the processor 610, the memory 620, the storage device 630, and input/output devices 640.

Although an example processing system has been described in FIG. 6, embodiments of the subject matter and the functional operations described above can be embodiments in other types of digital electronic circuitry, or in computer software, firmware, or hardware, including the structures disclosed in this specification and their structural equivalents, or in combinations of one or more of them. Embodiments of the subject matter described in this specification can be implemented as one or more computer program products, e.g., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example: B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')$_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the systems and techniques described herein have been presented. Nevertheless, it will be understood that various modifications may be made without departing from the spirit and scope of such system and techniques. Accordingly, other embodiments are within the scope of the following claims.

The invention claimed is:

1. An injection device comprising:
    a cartridge configured to hold a volume of fluid, the cartridge having a proximal end and a distal end through which the fluid is dispensed;
    a cartridge housing configured to hold the cartridge;
    a stopper disposed in the cartridge and configured to move from the proximal end to the distal end to cause the fluid to be dispensed through the distal end of the cartridge; and
    an electronic device disposed at the distal end of the cartridge, the electronic device comprising
        an emitter configured to transmit a signal through a portion of the cartridge housing toward the stopper,
        a receiver configured to receive reflections of the signal from the stopper,
        a controller configured to wirelessly transmit data related to a position of the stopper in the cartridge, and
        a clasp or snap portion configured to releasably attach the electronic device to the cartridge housing.

2. The injection device of claim 1, wherein the cartridge comprises a material that allows the signal and the reflections of the signal to pass through the cartridge.

3. The injection device of claim 2, wherein the material comprises a transparent material.

4. The injection device of claim 1, wherein the emitter is an acoustic device and the signal comprises acoustic waves.

5. The injection device of claim 1, wherein the emitter is an ultrasonic emitter and the signal comprises ultrasound waves.

6. The injection device of claim 1, wherein the emitter is a light emitter and the signal comprises light waves.

7. The injection device of claim 1, wherein the electronic device further comprises a battery electrically connectable to the electronic device.

8. The injection device of claim 7, wherein the battery is disposed in a housing of the injection device.

9. The injection device of claim 8, wherein the battery is electrically connected to the electronic device with electrical leads disposed in the cartridge housing.

10. The injection device of claim 9, wherein the electrical leads are disposed within a side wall of the cartridge housing.

11. The injection device of claim 1, where the electronic device further comprises a memory storage medium configured to store data related to a position of the stopper.

12. The injection device of claim 11, wherein the controller is configured to calculate a volume of dispensed fluid based on the data related to a position of the stopper.

13. The injection device of claim 1, wherein the emitter is configured to emit a signal at an angle between a minimum angle of 0 degrees and a maximum angle of between 0 and 90 degrees relative to a longitudinal axis of the cartridge.

14. The injection device of claim 1, wherein the emitter is configured to emit a signal at an angle between a minimum angle of 0 degrees and a maximum angle of between 20 and 70 degrees relative to a longitudinal axis of the cartridge.

15. The injection device of claim 1, wherein the emitter is configured to emit a signal at an angle of between a minimum angle of 0 degrees and a maximum angle of between 55 and 65 degrees relative to a longitudinal axis of the cartridge.

16. The injection device of claim 1, wherein an end of the stopper that faces the emitter and the receiver comprises a reflective material.

17. The injection device of claim 16, wherein the reflective material comprises a metal.

18. The injection device of claim 1, wherein the controller is configured to calculate a volume of fluid dispensed through the cartridge.

19. The injection device of claim 1, wherein the clasp or snap portion is configured to engage a ridge of the cartridge housing to secure the electronic device to the cartridge housing.

20. An injection device comprising:
- a cartridge configured to hold a volume of fluid, the cartridge having a proximal end and a distal end through which the fluid is dispensed;
- a cartridge housing configured to hold the cartridge, the cartridge housing having electrical leads disposed within a sidewall of the cartridge housing;
- a stopper disposed in the cartridge and configured to move from the proximal end to the distal end to cause the fluid to be dispensed through the distal end of the cartridge; and
- an electronic device disposed at the distal end of the cartridge, the electronic device comprising
  - an emitter configured to transmit a signal toward the stopper,
  - a receiver configured to receive reflections of the signal from the stopper, and
  - a controller configured to wirelessly transmit data related to a position of the stopper in the cartridge.

21. The injection device of claim 20, wherein the electronic device is integrated with a cartridge housing of the injection device.

22. The injection device of claim 20, wherein the electronic device is detachable from a cartridge housing of the injection device.

23. The injection device of claim 22, wherein the electronic device is configured to clip to the cartridge housing of the injection device.

24. The injection device of claim 20, further comprising a housing comprising a battery, wherein the electrical leads electrically connect the electronic device to the battery.

25. The injection device of claim 20, wherein the emitter and the receiver are disposed at diametrically opposite locations with respect to the cartridge.

* * * * *